US00PP21698P3

(12) United States Plant Patent
Brotzman et al.

(10) Patent No.: US PP21,698 P3
(45) Date of Patent: Feb. 8, 2011

(54) THORNLESS HONEYLOCUST TREE NAMED 'DRAVES'

(50) Latin Name: ***Gleditsia triacanthos* var. *inermis***
Varietal Denomination: Draves

(76) Inventors: Timothy C. Brotzman, 6899 Chapel Rd., Madison, OH (US) 44057; Thomas M. Draves, 1821 Sharrick Rd., Darien, NY (US) 14040

( * ) Notice: Subject to any disclaimer, the term of this patent is extended or adjusted under 35 U.S.C. 154(b) by 0 days.

(21) Appl. No.: 12/383,921

(22) Filed: Mar. 30, 2009

(65) Prior Publication Data

US 2010/0251441 P1 Sep. 30, 2010

(51) Int. Cl.
*A01H 5/00* (2006.01)

(52) U.S. Cl. ..... Plt./217

(58) Field of Classification Search ..... Plt./217

See application file for complete search history.

*Primary Examiner*—Annette H Para
(74) *Attorney, Agent, or Firm*—Renner, Otto, Boisselle & Sklar, LLP

(57) ABSTRACT

A thornless honeylocust tree named 'Draves', a medium tree distinguished by its strongly upright, columnar form.

3 Drawing Sheets

Latin name of the genus and species including the variety denomination of the plant claimed: The plant claimed relates to a new and distinct variety of thornless honeylocust tree, botanically known as *Gleditsia triacanthos* var. *inermis,* and known by the cultivar name 'Draves'.

This new cultivar was found growing on a cultivated, maintained residential property near Darien, N.Y. This new cultivar was noted as distinctive because of its strongly upright, columnar form.

The 'Draves' variety is the only variant of thornless honeylocust tree we are aware of that displays this strongly columnar form with a clearly defined central leader. The following selections of honeylocust trees, all broadly pyramidal and lacking a defined central leader, are offered for comparison: Fairview (not patented) 50'×40' (15.2×12.2 m) @ 15 yrs, Imperial® (Impcole U.S. Plant Pat. No. 1,605) 25'×24' (7.6 m×7.3 m) @ 15 yrs, Moraine (U.S. Plant Pat. No. 836) 32'×28' (9.8×8.5 m) @ 15 yrs, Perfection (not patented) 50'×30' (15.2 m×9.1 m), Shademaster® (U.S. Plant Pat. No. 1,515) 45'×35' (13.7 m×10.7 m), Skyline® (Skycole U.S. Plant Pat. No. 1,619) 45'×35' (13.7 m×10.7 m) and True-Shade® (not patented) 40'×35' (12.2 m×9.1 m) having height to width ratios as noted (Dirr, *Manual of Woody Landscape Plants,* $6^{th}$ edition, 2010).

The original 'Draves' cultivar, which is approximately 55 years old, is approximately 45' tall and 18' wide. Trunk diameter is approximately 13.5" at breast height. The crown/branching is full from bottom to top with moderate taper. No thorns/spines have been observed. Seed pods have been observed. Tree form is strongly excurrent with the leader outgrowing the lateral branches, producing a strongly columnar shape with upright-growing lateral branches and a clearly defined central leader. Compound leaves are dark, blue-green and lustrous, primarily bipinnately compound in character on vigorous growth. Otherwise they are pinnate.

The original 'Draves' cultivar bears no indications of disease sensitivity. Honeylocust Plant Bug has been observed. No observations have been made to other problems common to honeylocust trees, specifically canker, Spider Mites, Webworm or Midge Pod Gall.

The 'Draves' cultivar has been asexually reproduced at Brotzman's Nursery in Madison, Ohio by budding and grafting, and plants propagated by this method have displayed the same unique characteristics of the original plant.

Figure 1:
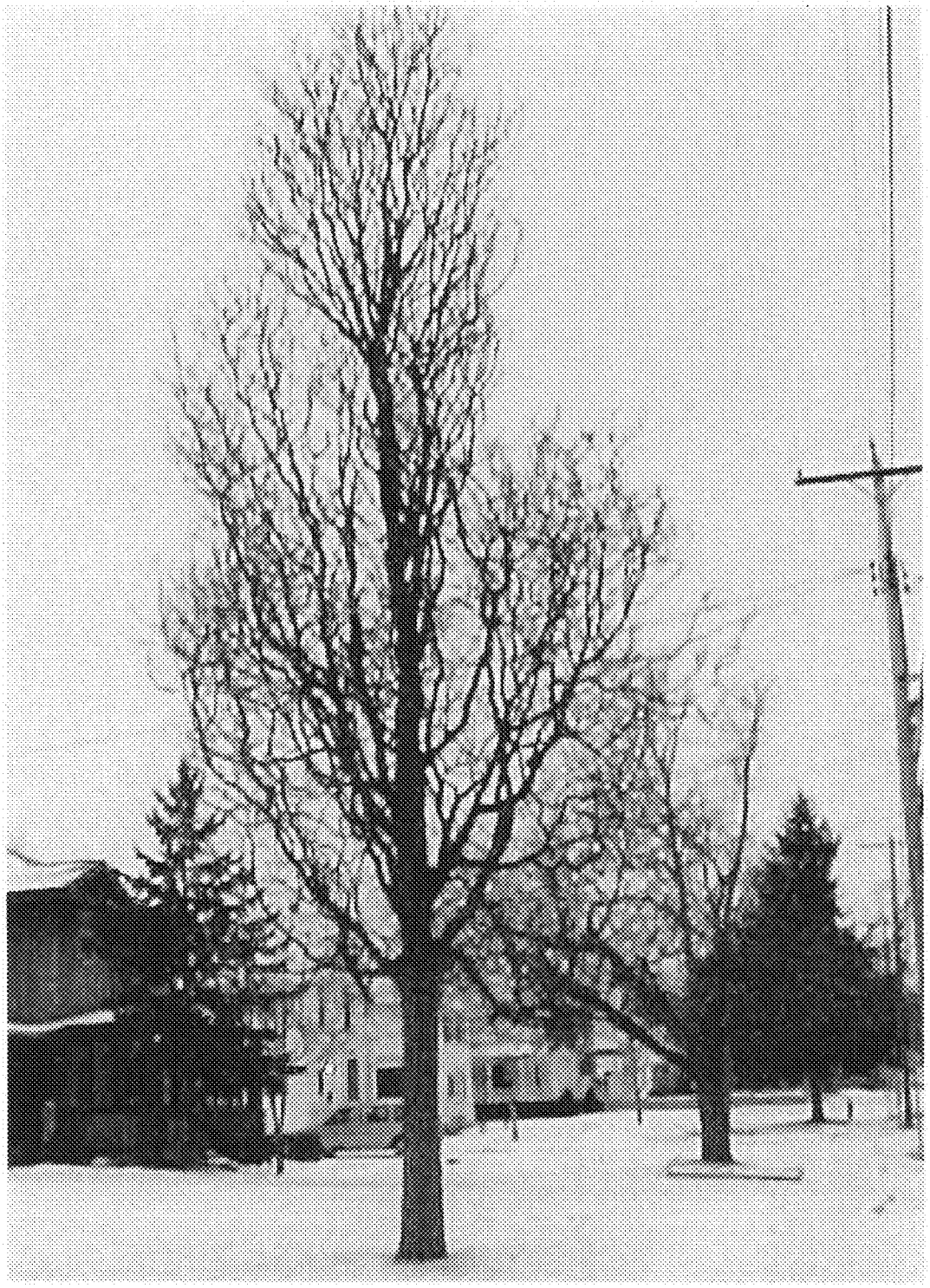
FIG. 1 is a colored photograph illustrating the overall appearance of the original cultivar 'Draves' in winter without leaves.
Figure 2:
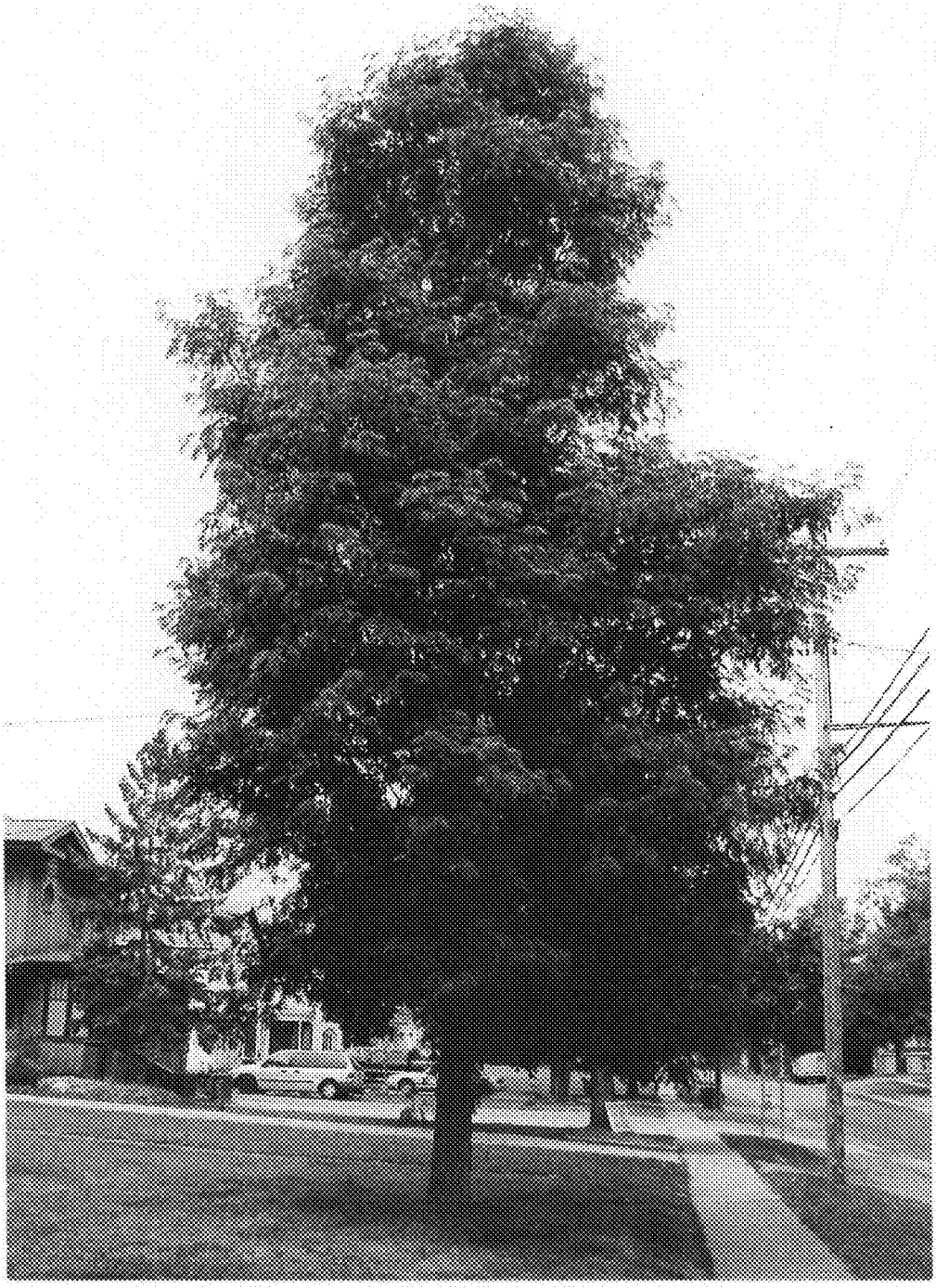
FIG. 2 is a colored photograph illustrating the overall appearance of the original 'Draves' in the summer.
Figure 3:
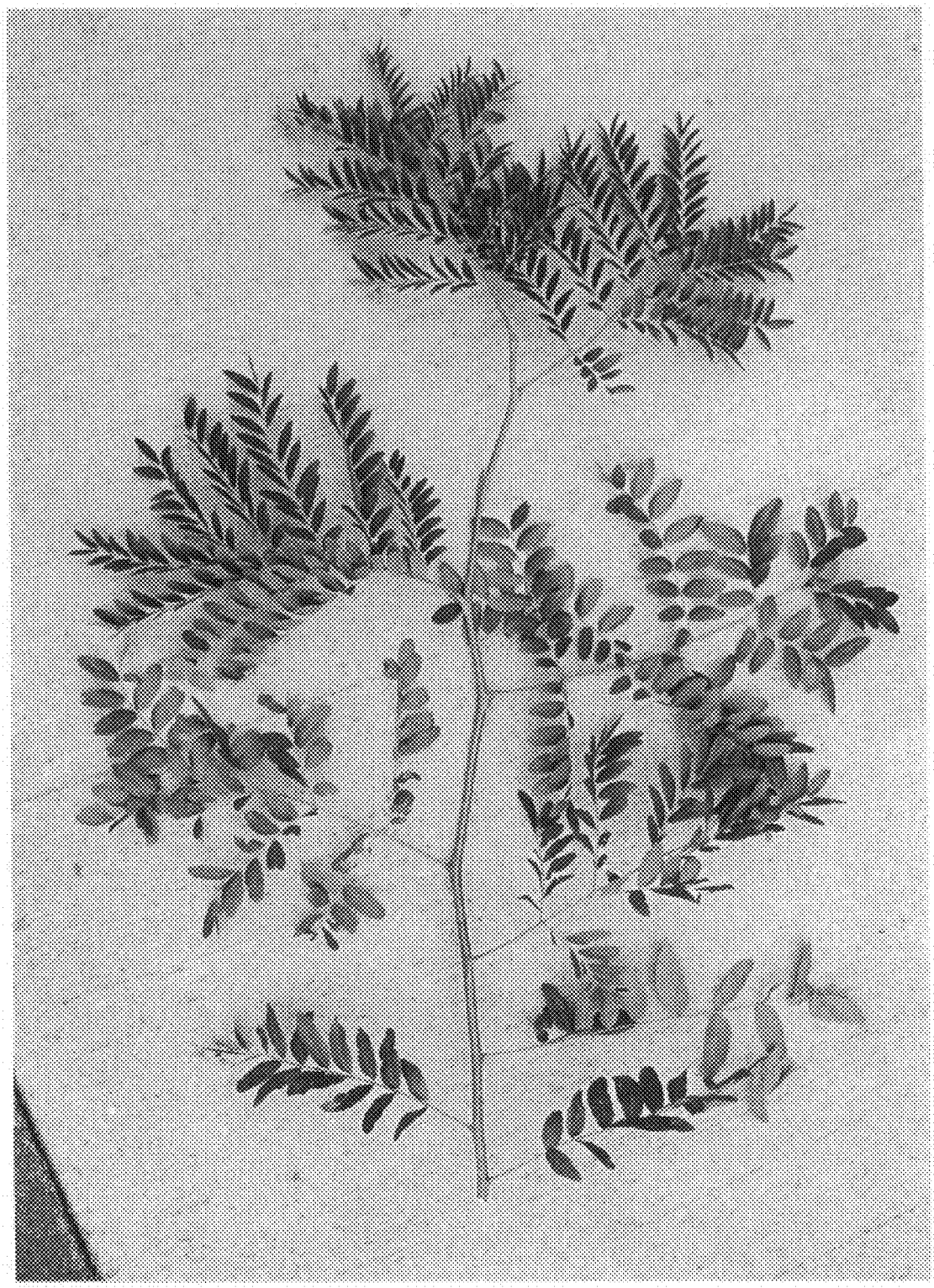
FIG. 3 is a colored photograph illustrating the new growth of 'Draves' in the summer.

All of the drawing figures show the colors as truly as is reasonably possible to obtain in colored reproductions of this type.

The following is a detailed description of my new cultivar, 'Draves'. In all cases, where color is different from the typical and is considered a distinguishing feature of this variety, reference is made to specific colors on The R.H.S. Colour Chart (1995 ed.) published by The Royal Horticultural Society, London, England. Here follows a detailed description of the characteristics of this cultivar, as displayed by the original tree, which is approximately 55 years old, growing on a cultivated, well maintained residential property near Darien, N.Y. Coloration of leaves and bark may be variable, due to conditions of nutrition, stress, age of plant, location on plant and the presence/absence of sun/shade. Plant part comparisons have been made using samples taken from the original tree where growth rates and characteristics are considered typical.

BOTANICAL DESCRIPTION

Parentage: Unknown—discovered growing on a cultivated, maintained residential property near Darien, N.Y.

Hardiness: Hardy in USDA Hardiness Zone 4.

Growth rate: Moderate, more rapid in youth. The original tree grows approximately 6-18"/year. One year whips can reach 6' (Boring, Oreg.) to 9' (Belvidere, Tenn.) under normal nursery conditions. Two and three year old plants have grown 2-4'/year under normal nursery conditions in Madison, Ohio.

Form: Strongly excurrent with the leader outgrowing the lateral branches, producing a strongly columnar shape with upright-growing lateral branches and a clearly defined central leader.

Habit: Central leader with densely arranged, lateral branches which display an upright orientation. Primary branches on the lower third of the trunk form an angle of approximately 45° with the trunk while those on the upper two-thirds of the trunk form angles of approximately 30°. Within 1.5' to 3.0' of the trunk, all of the primary branches are oriented such that they form an angle of approximately 30° with the trunk, which contributes to superior durability against winter storm damage. This is a unique and distinguishing feature of the 'Draves' variety. In addition, the 'Draves' variety exhibits branches which are far more slender and shorter than is typical for this specie. Eight primary lateral branches were measured on the original tree. Trunk diameter at the point of branch attachment was 13", and when measured 6" from their base at the branch collar, the 8 branches had an average diameter of 4.75", or 35% of the trunk diameter. Twelve secondary branches were measured 6" from their base with average diameters of 2.88", or 61% of the average primary branch diameter. The distinctly upright, columnar habit of the 'Draves' variety is further defined by secondary branches arising from the inside of the primary branches having a nearly vertical orientation. Secondary branches arising to the outside of the primary branches are ascending, but slightly less than vertical and angled outward.

Bark: Mature bark dark brown, Brown Group 200D.

Leaves: Pinnately compound with 8 to 20 oblong-lanceolate leaflets along the central axis, or bipinnately compound with 8 to 10 branches along a central rachis, each with 18-20 leaflets. Bipinnate leaves are most common on vigorous branches. Leaflets are 20 mm-30 mm long by 7 mm-12 mm wide, and are lustrous dark blue-green Yellow Green Group 147A. Autumn color is yellow, Yellow Group 12A. The base of the petiole is swollen and encloses the lateral bud.

Twigs: Show typical sympodial branching. New growth bright green Yellow Green Group 146A. Second year branches moderate to heavily lenticeled, darkening to Yellow Green Group 148A and Grey-Brown Group 199A on older branches until formation of thicker, dark brown bark.

Flowers: Not observed.

Seeds: Generally seedless, but some seed pods have been observed. Typical of the species, flat, twisted, approximately 10" long and 1" wide (25 cm.×2.5 cm). Depending on stage of maturity, pods change from green to brown, most closely resembling Gray-Red Group 181C and Yellow-Green Group 146D. Individual seeds are 0.28"×0.16" (7 mm×4 mm) shiny, Brown Group 200A.

Spines: Not observed.

We claim:

1. A thornless honeylocust tree named 'Draves', as described and illustrated, a medium tree distinguished by its strongly upright, columnar form.

* * * * *